(12) United States Patent
Bell, Jr.

(10) Patent No.: US 7,578,967 B2
(45) Date of Patent: Aug. 25, 2009

(54) STEAM COLLAPSING APPARATUS AND SYSTEM

(75) Inventor: James E. Bell, Jr., Lawrence, KS (US)

(73) Assignee: Continental Equipment Company, Inc., Lawrence, KS (US)

( * ) Notice: Subject to any disclaimer, the term of this patent is extended or adjusted under 35 U.S.C. 154(b) by 1123 days.

(21) Appl. No.: 10/374,127

(22) Filed: Feb. 25, 2003

(65) Prior Publication Data

US 2004/0166020 A1  Aug. 26, 2004

(51) Int. Cl.
*A61L 2/07* (2006.01)
*F16T 1/02* (2006.01)

(52) U.S. Cl. .................. 422/26; 422/295; 422/298; 122/442; 137/3; 137/11; 137/171; 137/179

(58) Field of Classification Search ............... 137/179, 137/396, 171, 11; 122/442
See application file for complete search history.

(56) References Cited

U.S. PATENT DOCUMENTS

| | | | |
|---|---|---|---|
| 97,405 A | 11/1869 | Hughes | |
| 838,314 A | 12/1906 | Fricke | |
| 1,624,066 A | 4/1927 | Petersen | |
| 1,960,914 A * | 5/1934 | McCoy | 261/77 |
| 2,899,014 A | 8/1959 | Sinex | |
| 3,009,537 A | 11/1961 | Glasgow et al. | |
| 3,371,469 A | 3/1968 | Murdock et al. | |
| 3,724,180 A | 4/1973 | Morton et al. | |
| 3,905,385 A | 9/1975 | Green | |
| 3,997,303 A | 12/1976 | Newton | |
| 4,096,876 A | 6/1978 | Ulrich | |
| 4,097,358 A | 6/1978 | Wiseman | |
| 4,146,775 A | 3/1979 | Kirchner et al. | |
| 4,149,557 A | 4/1979 | Keech et al. | |
| 4,261,950 A | 4/1981 | Bainbridge et al. | |
| 4,305,548 A | 12/1981 | Miner et al. | |
| 4,447,399 A | 5/1984 | Runnells et al. | |
| 4,456,173 A | 6/1984 | Miner et al. | |
| 4,468,962 A | 9/1984 | Keech et al. | |
| 4,508,135 A | 4/1985 | Schlesch et al. | |
| 4,509,965 A | 4/1985 | Morton | |
| 4,564,746 A | 1/1986 | Morton et al. | |
| 4,630,633 A | 12/1986 | Vallery | |
| 4,675,505 A | 6/1987 | Fischer | |
| 4,865,814 A | 9/1989 | Childress | |
| 4,879,902 A | 11/1989 | Loniello | |

(Continued)

OTHER PUBLICATIONS

Drane-Kooler Water tempering device, Installation, operation and maintenance manual, 2001 Brochure of Dristeem Humidifer Company.

(Continued)

*Primary Examiner*—Elizabeth L McKane
(74) *Attorney, Agent, or Firm*—Brian B. Diekhoff; Polsinelli Shughart PC (57) ABSTRACT

Apparatus and systems serve to collapse steam in effluent released from steam sterilizers and sterilizer systems. These systems include tanks or containers configured for receiving and holding fluids, for example, water, and include a fluid outlet and a port that receives the released effluent. A conduit extending into the tank from the effluent receiving port provides a path for the steam to the fluid in the tank, to collapse the steam.

63 Claims, 5 Drawing Sheets

U.S. PATENT DOCUMENTS

| | | | |
|---|---|---|---|
| 4,908,188 A | 3/1990 | Jefferis, III et al. | |
| RE33,414 E | 10/1990 | Morton | |
| 5,000,765 A | 3/1991 | Nelson | |
| 5,026,524 A | 6/1991 | Powell et al. | |
| 5,065,785 A | 11/1991 | Deacon et al. | |
| 5,099,823 A | 3/1992 | Nelson et al. | |
| 5,126,080 A | 6/1992 | Morton et al. | |
| 5,132,084 A * | 7/1992 | Harrell et al. | 422/110 |
| 5,199,486 A | 4/1993 | Balmer et al. | |
| 5,223,229 A | 6/1993 | Brucker | |
| 5,337,703 A | 8/1994 | Schlesch et al. | |
| 5,366,693 A * | 11/1994 | Burgos et al. | 422/110 |
| 5,370,085 A | 12/1994 | Dangreau | |
| 5,391,361 A | 2/1995 | Thakur et al. | |
| 5,429,800 A | 7/1995 | Miraldi et al. | |
| 5,516,466 A | 5/1996 | Schlesch et al. | |
| 5,761,069 A | 6/1998 | Weber et al. | |
| 5,880,438 A | 3/1999 | Parrini et al. | |
| 5,882,590 A | 3/1999 | Stewart et al. | |
| 5,894,014 A | 4/1999 | Houston et al. | |
| 5,942,163 A | 8/1999 | Robinson et al. | |
| 5,947,145 A | 9/1999 | Schlesch et al. | |
| 5,983,996 A | 11/1999 | Romero | |
| 5,992,436 A | 11/1999 | Hellman et al. | |
| 5,997,813 A * | 12/1999 | Yaskoff et al. | 422/26 |
| 6,086,822 A | 7/2000 | Trinidad | |
| 6,145,529 A | 11/2000 | Hellman et al. | |
| 6,279,593 B1 | 8/2001 | Sheppard | |
| 6,485,537 B2 | 11/2002 | Brilmaker | |
| 6,814,932 B2 | 11/2004 | Hlebovy et al. | |
| 6,875,399 B2 | 4/2005 | McVey | |
| 6,953,549 B2 | 10/2005 | Hill et al. | |
| 6,992,494 B2 | 1/2006 | Kaiser et al. | |
| 2001/0021372 A1 | 9/2001 | Omtveit et al. | |
| 2001/0045674 A1 | 11/2001 | Herr | |
| 2002/0121303 A1 | 9/2002 | Sheely | |
| 2002/0124666 A1 | 9/2002 | Navarro et al. | |
| 2002/0139096 A1 | 10/2002 | Brilmaker | |
| 2003/0025093 A1 | 2/2003 | Kenny et al. | |
| 2003/0074981 A1 | 4/2003 | Rebik | |
| 2005/0125105 A1 | 6/2005 | Halstead et al. | |
| 2006/0073077 A1 | 4/2006 | Centanni | |

OTHER PUBLICATIONS

Drane Kooler™ tempering device brochure by Dri Steem Humidifier Company, 1 page.

TempR-Drain™ for condensate cooling Bulletin No. 578 by Armstrong, 2 pages, Jun. 1999.

Armstrong Humidifiers, Cool that Condensate, http://www.armstrong-intl.com, copyright 2003 (2 pages).

* cited by examiner

STEAM COLLAPSING APPARATUS AND SYSTEM

TECHNICAL FIELD

The present invention relates to apparatus and systems for collapsing steam and tempering drain water, and in particular, to apparatus and systems for use with steam sterilizers and steam sterilizer systems that employ these apparatus.

BACKGROUND

Figure 1:
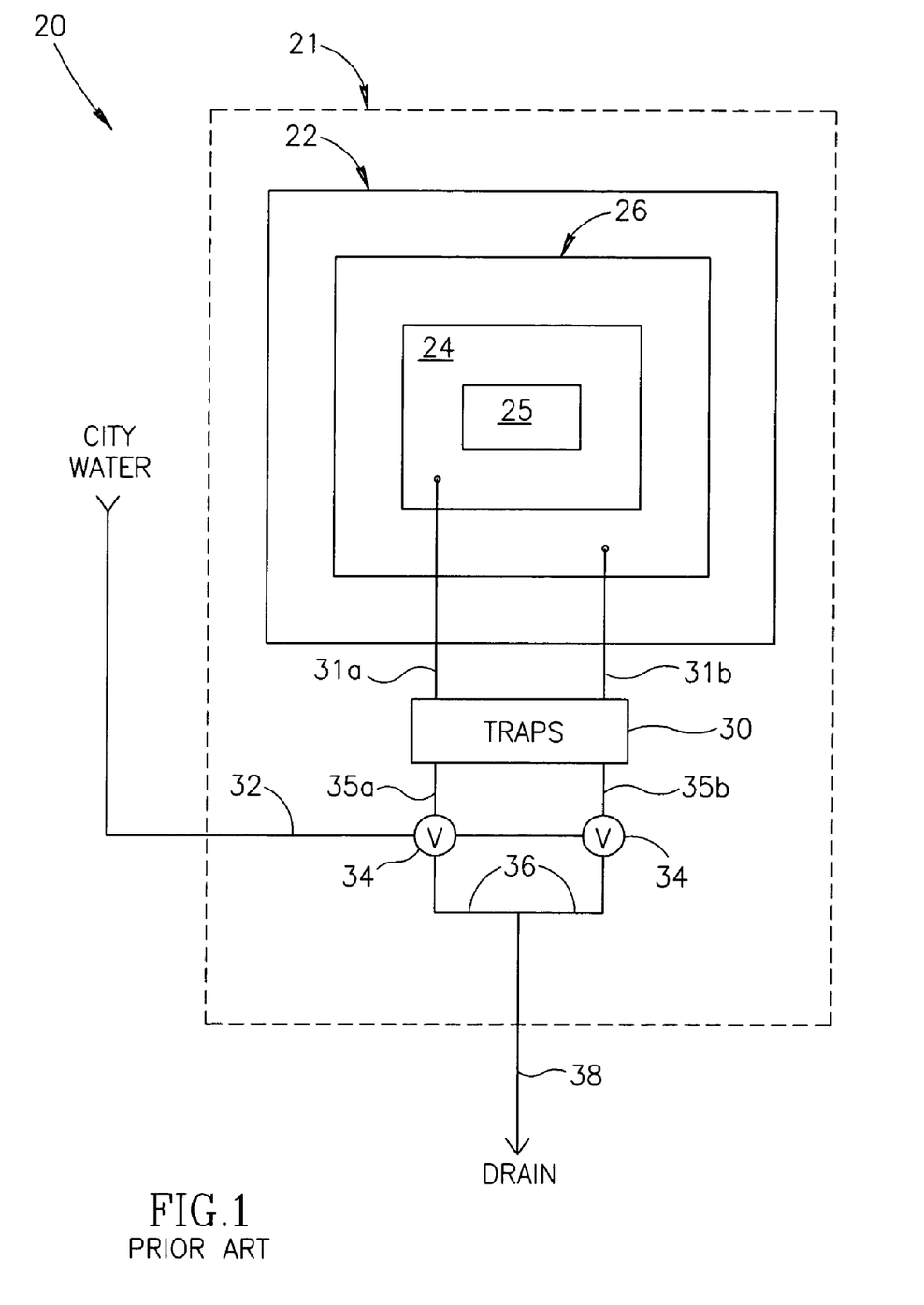
FIG. 1 is schematic diagram of a contemporary sterilizer and drainage system.

In steam sterilizers used in hospitals, universities, and other institutional facilities, where it is necessary to sterilize equipment, steam can be used to perform the sterilization. An exemplary sterilization system 20, for example, as shown in FIG. 1 has a sterilizer system 21 including a sterilizer 22 formed of a sterilization chamber 24 into which the components 25 are put, and an outer jacket 26 around the chamber 24 for warming and insulating the sterilization chamber 24. Steam is introduced into the jacket 26 to insulate and heat the chamber 24, and separately into the chamber 24 to sterilize the components 25. The steam from the jacket 26 and chamber 24 is collected in steam traps 30 (over lines 31a, 31b) that provide steam condensate toward a drain.

Building codes typically specify that water provided from equipment to a drain not be hotter than a certain temperature, such as 140 degrees Fahrenheit (F) (60 degrees Celsius), to minimize damage to the pipes and leaching of heavy metals. Consequently, the steam and its condensate must be cooled before it is provided down the drain.

In this system 20, typical of contemporary systems for sterilizers, the steam condensate provided from the steam traps 30 is mixed with cooling water from a cool water line 32, typically a municipal water line. The flow in this cool water line 32 is controlled by valves (v) 34, typically needle valves, connected to the traps 30 over lines 35a, 35b. The mixed water and steam condensate is then mixed and passed through lines 36 to the drain line 38 at a temperature, sufficiently cool (below 140 degrees F.), to be in accordance with building codes.

The cool water line 32 coupled with the needle valves 34, typically provides cooling water continuously at a rates of 0.5 to 5 gallons per minute, depending on the particular sterilizer system. This cooling water typically runs continuously. Accordingly, substantial amounts of water are wasted, and in many cases going unused, passing straight out of the sterilization system 20 to the drain.

SUMMARY

The present invention is directed to an apparatus and a system that reduces water wasting, when compared to contemporary sterilizer systems. The apparatus of the invention eliminates the need for needle or other valves in sterilizers or sterilizer systems and, thus reduces the cool water from running constantly, so as to conserve water. The apparatus can be combined with conventional sterilizers and/or sterilizer systems to collapse steam from these sterilizers and/or sterilizer systems and provide it to a drain line or drain at a temperature sufficiently cool in accordance with building codes (typically less than 140 degrees F.).

An embodiment disclosed is directed to an apparatus for collapsing steam. The apparatus has a container, for example, a tank, configured for holding fluid, for example, water. The container includes at least one inlet port, at least one drain port, and at least one effluent receiving port. There is a conduit extending from the at least one effluent receiving port into the container, with the conduit configured for providing a path for steam in an effluent to the fluid, in the container to collapse the steam.

Another embodiment disclosed is directed to a sterilization system having a sterilizer system coupled to a steam collapsing system. The sterilizer system has a steam sterilizer including a sterilizing chamber for holding components to be sterilized, and an outlet through which an effluent including steam is emitted. The steam collapsing system includes a container, for example, a tank, configured for receiving and holding fluid, for example, water, with the container including a fluid outlet and at least one port in communication with the outlet of the steam sterilizer for receiving the effluent. A conduit extends from the at least one effluent receiving port into the container, with this conduit configured for providing a path for steam in the effluent to the fluid in the container, to collapse the steam.

Another embodiment is directed to a steam collapsing system. This system includes a container, for example, a tank, configured for receiving and holding fluid, typically water, and more particularly cooling or cool water from a municipal or other external source. The container also has a fluid outlet and at least one port for receiving effluent. A conduit extends from the at least one effluent receiving port into the container, and the conduit is configured for providing a path for steam in the effluent to the fluid in the container, in order to collapse the steam.

Also disclosed is a method for collapsing steam. This method includes providing a container, for example, a tank, for holding cooling water or fluid, the container including an effluent receiving port and a conduit in communication with this effluent receiving port. The conduit is configured for providing a pathway from the effluent receiving port to the cooling water. Cooling water is also provided to the container. Steam is then received in the container through the effluent receiving port, and this introduced steam moves along the pathway into contact with the cooling water, to collapse and become condensate.

BRIEF DESCRIPTION OF THE DRAWINGS

Attention is now directed to the drawings, where like numerals and characters indicate like or corresponding components. In the drawings.

DETAILED DESCRIPTION OF THE DRAWINGS

Figure 2:
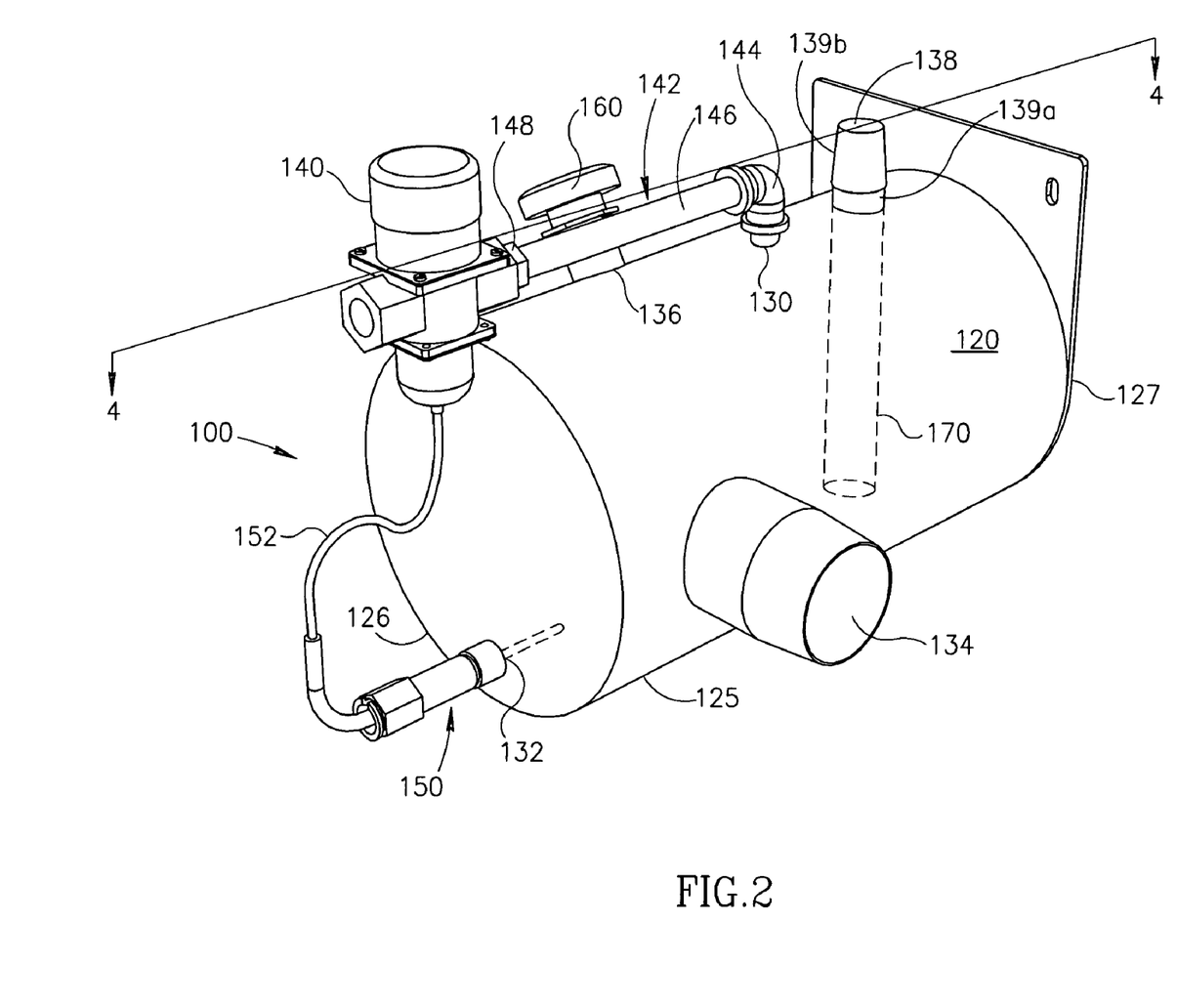
FIG. 2 is a perspective view of an embodiment of an apparatus present invention.
Figure 3:
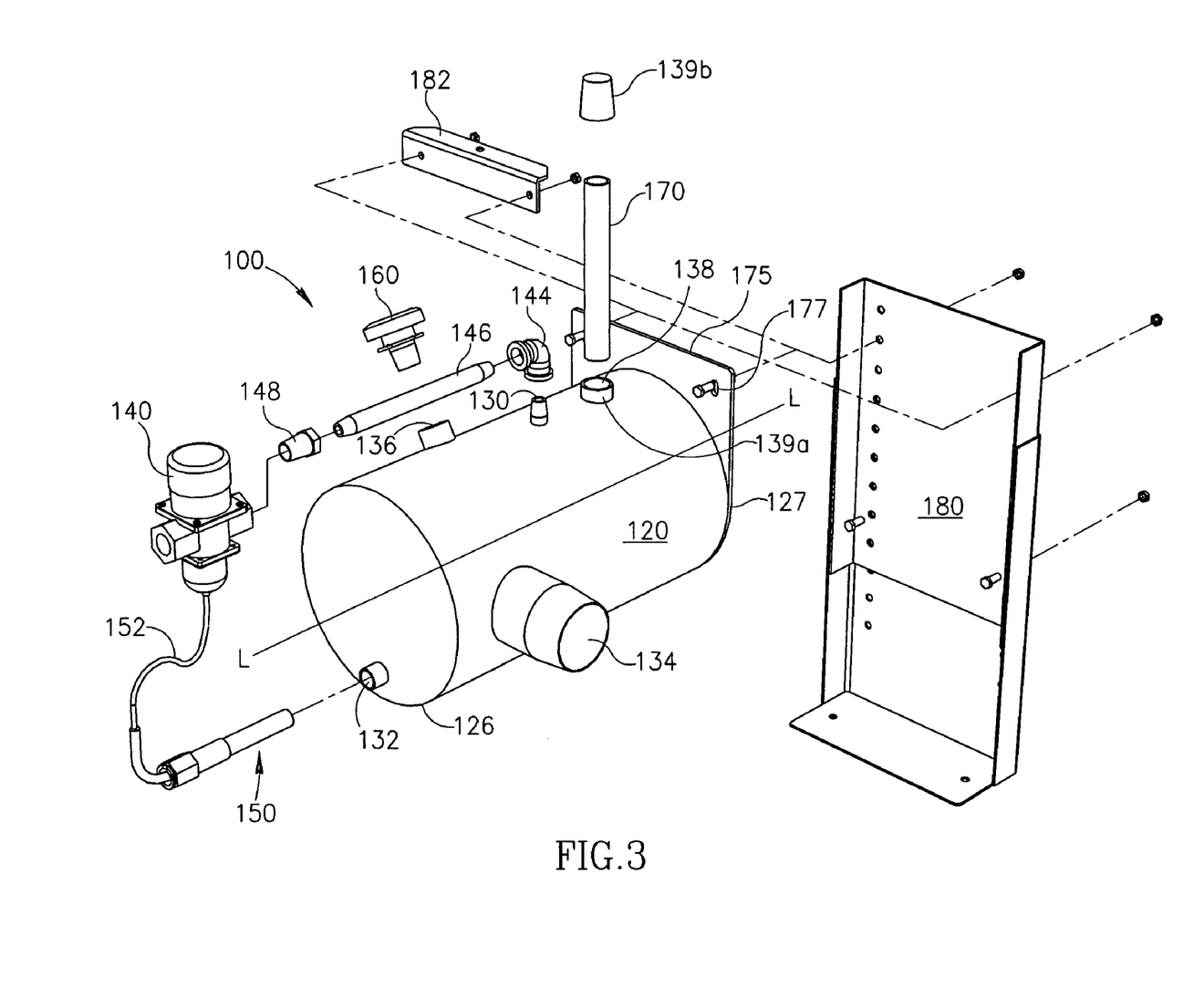
FIG. 3 is an exploded view of the apparatus of FIG. 2.
Figure 4:
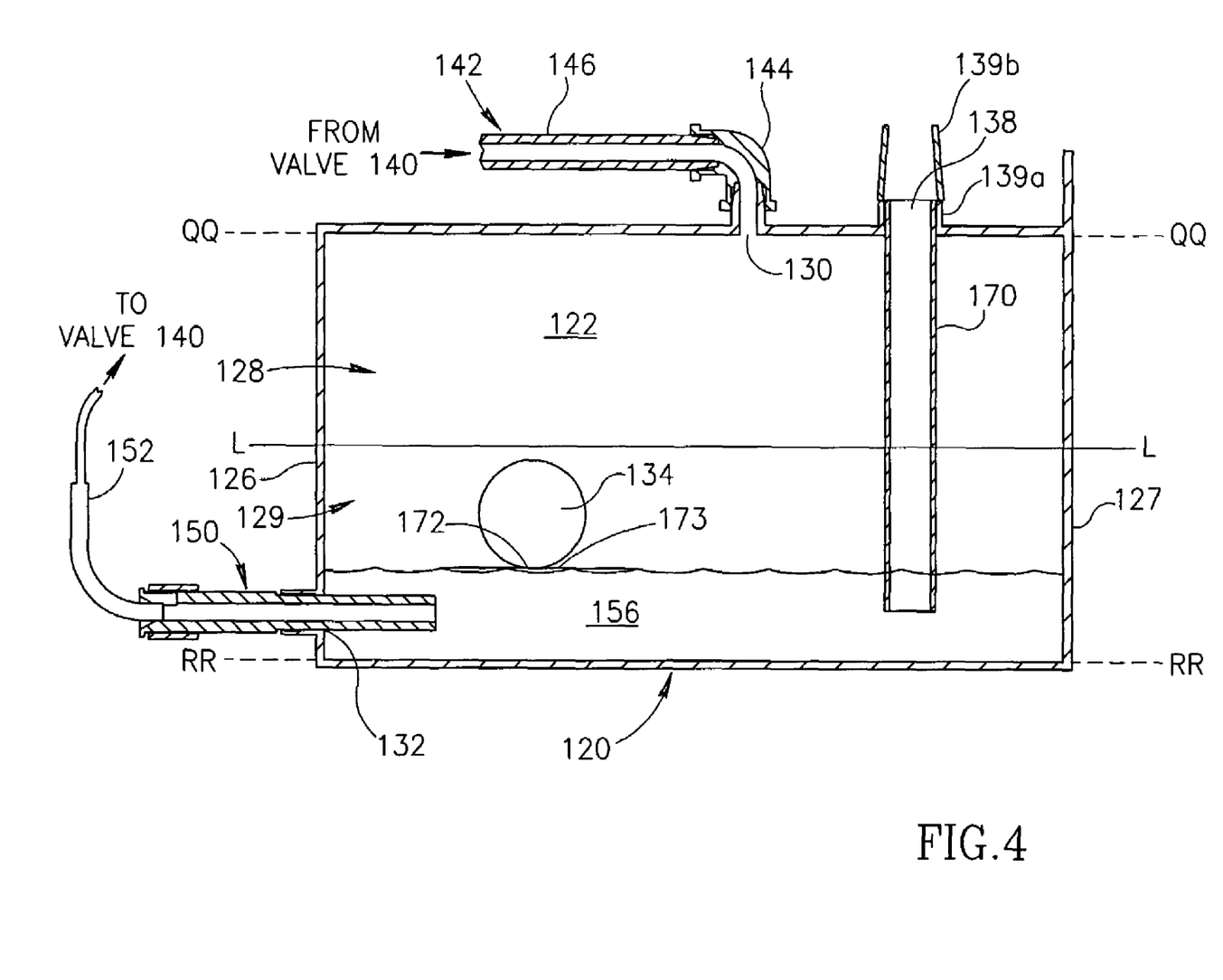
FIG. 4 is a cross-sectional view of the apparatus of FIG. 2 taken along line 4-4 with the valve and vent port not shown.

FIGS. 2-4 show the apparatus 100 of the present invention. The apparatus 100 includes a tank or container 120, having an inner chamber 122. The tank 120 and inner chamber 122 are typically cylindrical in shape, formed of a body portion 125 and ends 126, 127. The apparatus 100, including the tank 120 and chamber 122 are shown in a typical orientation, and this is exemplary only. To describe the apparatus 100 in this typical orientation, the tank 120, and in particular, the chamber 122, are divided into an upper section 128, and a lower section 129 by a longitudinal axis L. The uppermost point on the chamber 122 in the tank 120 is line QQ in broken lines, while the lowermost point on the chamber 122 in the tank 120 is the line RR in broken lines.

The tank 120 includes ports 130, 132, 134, 136 and 138. These ports 130, 132, 134, 136 and 138, include openings into the chamber 122 of the tank 120, through which water, steam, steam condensate, and/or other effluents enter and/or leave the tank 120 as described below. While single ports 130, 132, 134, 136 and 138 are shown, this is exemplary only, as multiple ports with their associated instrumentation (as detailed below) are also permissible.

An inlet port 130 is located on the upper section 128 of the tank 120 and typically connects with a valve 140, for example, a mechanical temperature actuated valve, through a conduit 142. The conduit 142 is typically formed of an elbow 144, a tube 146 and a bushing 148, this bushing 148 connecting to the valve 140. The valve 140 connects to a line 242 (FIG. 5) that typically receives water from a municipal or other external source. This port 130 is typically located at the highest point on the tank 120 (in correspondence with line QQ), but could be positioned anywhere on the upper section 128 of the tank 120, and even at the lower section 129 of the tank 120, provided it is above the drain port 134.

A temperature probe (temperature sensor) 150 extends into a port 132 at the lower section 129 of the tank 120. This temperature probe 150 typically functions continuously, and is in communication with the valve 140 through the line 152. This line 152 is for example, a capillary tube, through which pressure increases/decreases therein, from the temperature actuated valve, to open/close the valve 140.

The temperature probe 150 is positioned to remain below the level 154 of the fluid, typically water 156, in the tank chamber 122, so as to measure water temperature in the tank 120. Should the temperature be above a predetermined level, for example, 140 degrees F., the temperature probe 150 will cause the valve 140 to open, allowing cooling water into the tank 120, through the port 130.

A drain port 134 is at the lower section 129 of the tank 120. Water exits the tank 120 through this drain port 134, where it goes to a drain and typically into the municipal drainage system. The position of the drain port 134 typically determines the fluid level 154 in the chamber 122 of the tank 120.

A vent port 136 typically is at the upper section 128 of the tank 120. This vent port 136 is typically capped by a vacuum relief valve 160. This valve 160 is typically adjusted to allow for venting of the tank 120 should there be a pressure build up in the chamber 122. This valve 160 may be manually or automatically activated. As stated above, while one port 136 and relief valve 160 are shown, this is exemplary only, as multiple ports/relief valves are permissible. All of the vent ports/relief valves should be positioned above the drain port 134, so as not to fill with water.

Figure 5:
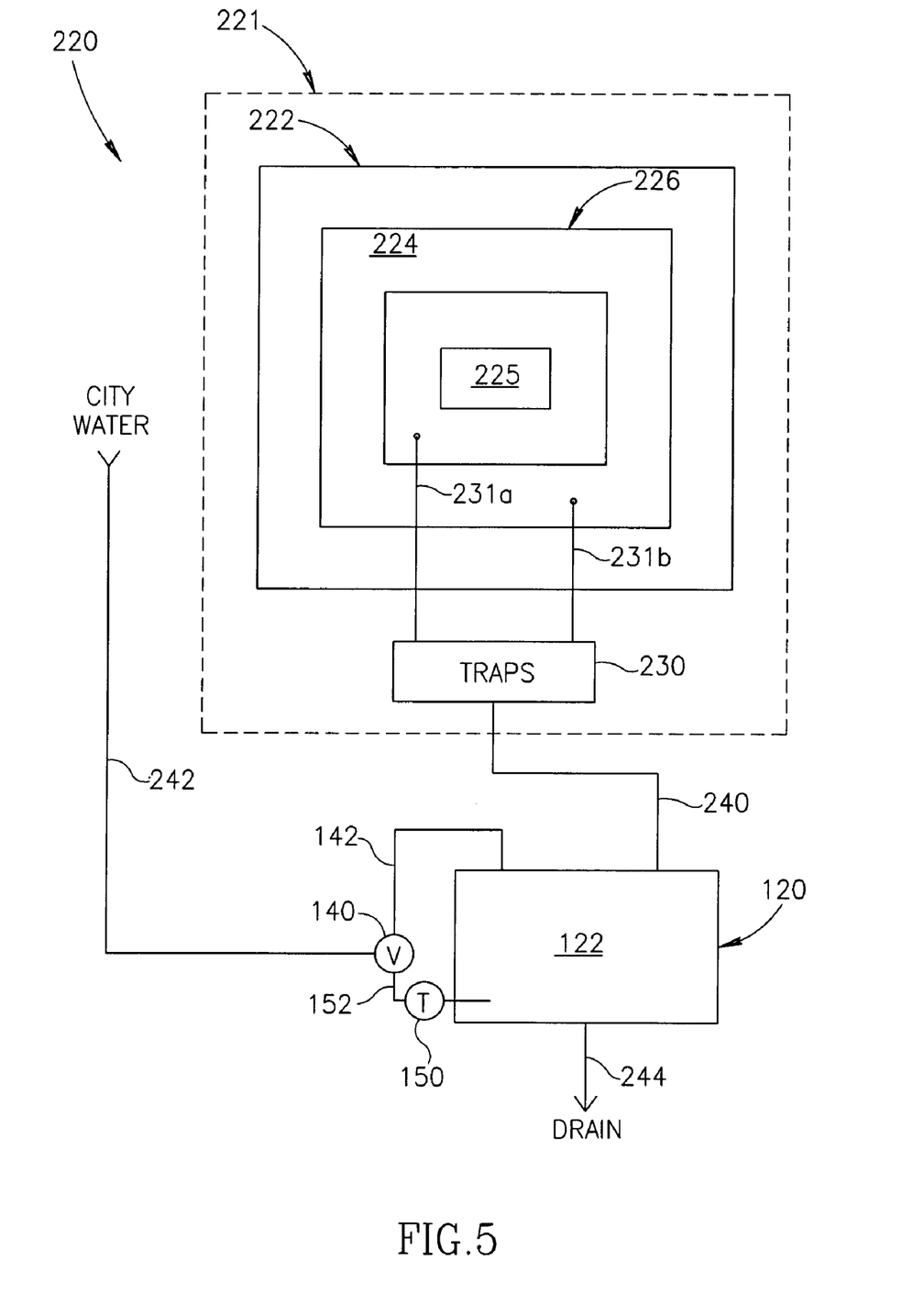
FIG. 5 is a schematic diagram of the apparatus of the present invention in a sterilizer system in accordance with an embodiment of the invention.

The effluent (or effluent receiving) port 138 is also at the upper section 128 of the tank 120. It is typically at the uppermost point of the tank 120 (corresponding to line QQ). The port 138 is typically formed from a stub 139a and a cap 139b. This port 138 receives steam, steam condensate, and/or other effluents from a sterilizer or sterilizer system, collectively "effluent", through a line 240 (FIG. 5). This line 240 is typically from steam trap or other outlet, of a sterilizer or sterilizer system.

A conduit 170 extends from this port 138 into the lower section of the chamber 122 of the tank 120. The conduit 170 extends to a point below the lowest point 172 (along tangent line 173) of the drain port 136, and typically is positioned to extend below the fluid level 154, to a point intermediate the lowermost point of the drain port 136 and the lowermost point of the chamber 122 (line RR). This intermediate point can be, for example, at least halfway into the fluid level 154 (for example, at a midpoint between lines 173 and RR). By extending into the water 156, the conduit 170 functions to collapse steam in the effluent by providing a path for the steam to the water 156 in the chamber 122 of the tank 120.

The tank 120 typically includes an extension 175 from its end 127. This extension typically includes openings 177 that allow the tank 120 to be fixed to a support member 180, typically with a suspension mount hangar 182. This support member 180 typically mounts the apparatus 100 as part of a sterilization system 220, as shown in FIG. 5. For example, the apparatus 100 can be mounted on a chassis or other similar support member. Other mounting arrangements are also suitable.

The tank 120 is typically made of materials such as stainless steel, or other materials suitable for handling high temperatures that do not leach heavy metals or other components. The body 125 and ends 126, 127, are typically joined together by welding or the like. The conduit 170 is typically a tube, for example a cylindrical tube, although other shapes are permissible, and made of materials such as stainless steel or other materials as described for the tank 120 above. The conduit 170 is typically attached to the port 138, at the stub 139a, by techniques such as welding and the like.

The tank 120, while typically cylindrical in shape, can also be any other shape, suitable for holding fluid. The tank 120 is typically of an internal volume large enough to handle all effluent (steam, steam condensate and other effluents) from the associated sterilizer or sterilizer system. However, the internal volume should be small enough to allow for flushing of the internal volume of the tank 120. For example, one embodiment of the tank 120 can be a cylindrical shaped tank with an approximately 6 inch (15.2 cm) diameter and an approximately 10 inches (25.4 cm) in length. In this example embodiment, the conduit 170 can be a cylindrical tube, approximately 1 inch (2.5 cm) in diameter and approximately 5 inches (12.7 cm) in length.

Turning to FIG. 5, the apparatus 100 is shown schematically as part of a sterilization system 220, that includes a sterilizer system 221. Here, the sterilizer system 221 includes a sterilizer 222, that is similar to the sterilizer 22 (detailed above), with similar components in the sterilizer system 221 and sterilizer increased by "200" from those in shown in FIG. 1 and described above. Here, the effluent, that includes steam, from the steam traps 230/sterilizer system 221/sterilizer 222 enters the tank 120 of the apparatus 100 through a line 240. This line 240 connects at the effluent receiving port 138. A line 242, typically for water, is attached to a municipal or external source (here for example, "city water"), is fed to the tank 120 of the apparatus 100, as regulated by the valve 140. A drain line 244 connects to the tank 120 at the drain port 134, for carrying fluid from the tank 120 to the drain.

FIGS. 2-5 will now be discussed in an exemplary operation of the apparatus 100, where stream is received from an outlet (s), collapsed in the apparatus 100, and released into a drain. In describing this exemplary operation, only the steam of the effluent will be specifically mentioned, and also the fluid in the chamber 122 of the tank 120 for collapsing the steam is water. Initially, steam is released from the traps 230 or other outlet(s), and enters the effluent (effluent receiving) port 138. This steam enters the conduit 170, where it travels a path so as to contact water 156 in the chamber 122 of the tank 120.

Within the chamber 122, the water 156 has been provided to it, to be at the level 154, corresponding to the lowest point 172 of the drain port 136.

The steam travels downward in the conduit 170, to contact the water 156 at the level 154. This contact collapses the steam into condensate, and this steam condensate, now added to the water present in the chamber 122, will typically raise the water temperature, that will be detected by the temperature probe (T) 150.

If the detected temperature is at or higher than a predetermined or threshold temperature, for example 140 degrees F., in accordance with building codes, the temperature probe 150 senses this elevated temperature. Pressure in the capillary tube 152 is increased, opening the valve (V) 140, allowing for water, typically cold or cool water, to enter the chamber 122, for cooling the steam/effluent. This cooled steam effluent becomes condensate, upon contacting the cool water. The temperature probe 150 works continuously, such that the valve 140 remains open until the water temperature in the chamber 122 is below the predetermined threshold. Once the fluid (e.g., water) in the chamber 122 of the tank 120 is below the threshold or predetermined temperature, the temperature probe 150 senses this temperature and decreases the pressure in the capillary tube 152. The pressure decrease causes the valve 140 to close, such that the flow of cooling water into the chamber 122 from the conduit 142 stops. The now cooled and collapsed steam (now condensate), mixed with the water 156 in the chamber 122 of the tank 120, exits the tank 120 and goes to a drain, through the drain line 244.

There has been shown and described at least one preferred embodiment of an apparatus and system for collapsing stream and steam condensate. It is apparent to those skilled in the art, however, that many changes, variations, modifications, and other uses and applications for the above-described apparatus and system, including its components are possible, and also such changes, variations, modifications, and other uses and applications which do not depart from the spirit and scope of the invention are deemed to be covered by the invention, which is limited only by the claims which follow.

What is claimed is:

1. An apparatus for collapsing steam comprising:
    a container configured for holding fluid comprising:
        at least one inlet port;
        a valve in communication with said at least one inlet port;
        at least one drain port configured to provide a drain path to a drain; and
        at least one receiving port; and
    a conduit extending from said at least one receiving port into said container and configured to convey steam to the fluid in said container to collapse the steam, wherein said container includes an uppermost point and a lowermost point, and said at least one drain port is intermediate said uppermost point and said lowermost point, wherein said at least one receiving port is above said at least one drain port;
    a temperature probe extending into said container and in communication with said valve, said temperature probe configured for sensing fluid temperatures; and
    wherein said temperature probe extends into said container intermediate said at least one drain port and said lowermost point.

2. The apparatus of claim 1, wherein said at least one inlet port is above said at least one drain port.

3. The apparatus of claim 1, wherein said conduit extends into said container at least to a level of said at least one drain port.

4. The apparatus of claim 1, wherein said valve is a controllable valve.

5. The apparatus of claim 4, wherein said valve is a temperature actuated valve.

6. The apparatus of claim 1, wherein said valve is configured for communication with at least one line from an external fluid source.

7. The apparatus of claim 1, wherein said container additionally includes:
    at least one vent port positioned above said at least one drain port.

8. The apparatus of claim 7, wherein said at least one vent port includes one vent port.

9. The apparatus of claim 1, wherein said container is cylindrical in shape.

10. The apparatus of claim 9, wherein said container includes an interior chamber of a shape corresponding to that of said container.

11. The apparatus of claim 1, wherein said at least one inlet port includes one inlet port.

12. The apparatus of claim 1, wherein said at least one drain port includes one drain port.

13. The apparatus of claim 1, wherein said at least one receiving port includes one receiving port.

14. A method for collapsing steam comprising:
    providing a container for holding fluid comprising a receiving port, a conduit extending from said receiving port into said container, at least one inlet port, a valve in communication with said at least one inlet port, and at least one drain port configured to provide a drain path to a drain; wherein the conduit is configured to convey steam to the fluid in said container to collapse the steam, wherein said container includes an uppermost point and a lowermost point, and said at least one drain port is intermediate said uppermost point and said lowermost point, wherein said at least one receiving port is above said at least one drain port;
    a temperature probe extending into said container and in communication with said valve, said temperature probe configured for sensing fluid temperatures;
    wherein said temperature probe extends into said container intermediate said at least one drain port and said lowermost point;
    providing fluid to said container; and
    receiving steam into said container through said conduit and into contact with the fluid to collapse the steam into condensate.

15. The method of claim 14, wherein providing said fluid comprises providing cooling water.

16. The method of claim 15, additionally comprising:
    sensing the temperature of the combined cooling water and condensate; and
    causing said valve to control the flow of cooling water into said container based on said sensed temperature.

17. The method of claim 16, wherein causing said valve to control the flow of cooling water into said container comprises opening said valve when a threshold temperature is sensed.

18. The method of claim 17, wherein causing said valve to control the flow of cooling water into said container comprises closing said valve when a return to below said threshold temperature is sensed.

19. The method of claim 17, wherein sensing the temperature of the combined cooling water and condensate is performed continuously.

20. A sterilization system comprising:
    a sterilizer system comprising:

a steam sterilizer comprising a sterilizing chamber for holding components to be sterilized; and
a sterilizer outlet through which at least steam is emitted; and
a steam collapsing system comprising:
a container configured for receiving and holding fluid comprising a fluid outlet and at least one receiving port in communication with said sterilizer outlet for receiving said at least steam; and
a conduit extending from said at least one receiving port into said container and configured to convey said at least steam to the fluid in said container to collapse said at least steam, wherein said container comprises at least one inlet port, and said fluid outlet comprises at least one drain port, wherein said container includes an uppermost point and a lowermost point, and said at least one drain port is intermediate said uppermost point and said lowermost point, wherein said at least one receiving port is above said at least one drain port.

21. The system of claim 20, wherein said at least one inlet port is above said at least one drain port.

22. The system of claim 21, wherein said steam collapsing system comprises a valve in communication with said at least one inlet port.

23. The system of claim 22, wherein said valve is a controllable valve.

24. The system of claim 23, wherein said valve is a temperature actuated valve.

25. The system of claim 22, wherein said valve is configured for communication with at least one line from an external fluid source.

26. The system of claim 22, wherein said steam collapsing system comprises a temperature probe extending into said container and in communication with said valve, said temperature probe configured for sensing fluid temperatures.

27. The system of claim 26, wherein said temperature probe extends into said container intermediate said at least one drain port and said lowermost point.

28. The system of claim 20, wherein said conduit extends into said container at least to a level of said at least one drain port.

29. The system of claim 20, wherein said container includes:
at least one vent port positioned above said at least one drain port.

30. The system of claim 20, wherein said container is cylindrical in shape.

31. The system of claim 30, wherein said container includes an interior chamber of a shape corresponding to that of said container.

32. The system of claim 30, wherein said at least one vent port includes one vent port.

33. The system of claim 20, wherein said at least one inlet port includes one inlet port.

34. The system of claim 20, wherein said at least one drain port includes one drain port.

35. The system of claim 20, wherein said at least one receiving port includes one receiving port.

36. A steam collapsing system comprising:
a container configured for receiving and holding fluid, said container including a fluid outlet and at least one port for receiving effluent; and
a conduit extending from said at least one effluent receiving port into said container, said conduit configured for providing a path for steam in said effluent to the fluid in said container to collapse the steam, wherein said container includes at least one inlet port, a valve in communication with said at least one inlet port, wherein said valve is a controllable valve, and said fluid outlet includes at least one drain port, wherein said container includes an uppermost point and a lowermost point, wherein said container includes a temperature probe extending into said container and in communication with said valve, said temperature probe configured for sensing fluid temperatures, said temperature probe extends into said container intermediate said at least one drain port and said lowermost point, and said at least one drain port is intermediate said uppermost point and said lowermost point, wherein said container includes at least one vent port positioned above said at least one drain port.

37. The system of claim 36, wherein said at least one inlet port is above said at least one drain port.

38. The system of claim 36, wherein said valve is a temperature actuated valve.

39. The system of claim 36, wherein said valve is configured for communication with at least one line from an external fluid source.

40. The system of claim 36, wherein said container is cylindrical in shape.

41. The system of claim 40, wherein said container includes an interior chamber of a shape corresponding to that of said container.

42. The system of claim 36, wherein said at least one inlet port includes one inlet port.

43. The system of claim 36, wherein said at least one drain port includes one drain port.

44. The system of claim 36, wherein said at least one vent port includes one vent port.

45. The system of claim 36, wherein said at least one effluent receiving port includes one effluent receiving port.

46. A sterilization system comprising:
a sterilizing chamber;
a steam collapsing system to receive steam from the sterilizing chamber, the steam collapsing system comprising:
a container configured for receiving and holding fluid, said container including at least one drain port and at least one port for receiving effluent; and
a conduit extending from said at least one effluent receiving port into said container, said conduit configured for providing a path for steam in said effluent to the fluid in said container to collapse the steam, wherein said container includes an uppermost point and a lowermost point, and said at least one drain port is intermediate said uppermost point and said lowermost point, wherein said effluent receiving port is above said at least one drain port, wherein said conduit extends into said container at least to said at least one drain port.

47. A method for collapsing steam from a steam sterilizer comprising:
providing a steam sterilizer;
providing a container comprising a chamber for holding fluid, a receiving port, and an outlet port;
providing a tube extending from said receiving port into said chamber, said tube in communication with the steam sterilizer;
providing fluid to said chamber;
receiving at least steam through said tube into contact with the fluid to collapse said at least steam to condensate; and
allowing at least some fluid and condensate from collapsed steam to move out of said chamber through said outlet port;

sensing the temperature of the combined fluid and condensate with a thermometer; and causing a valve to control the flow of additional fluid into said chamber based on said sensed temperature, wherein causing said valve to control the flow of additional fluid into said chamber includes opening said valve when said sensed temperature has increased to reach at least a predetermined temperature.

48. The method of claim 47, wherein said fluid comprises water.

49. The method of claim 48, wherein said predetermined temperature is approximately 140 degrees F.

50. The method of claim 47, wherein causing said valve to control the flow of additional water into said chamber includes closing said valve when said sensed temperature is below said predetermined temperature.

51. The method of claim 47, wherein sensing the temperature of the combined water and condensate includes continuously sensing the temperature of the combined water and condensate.

52. The method of claim 47, wherein said predetermined temperature is approximately 140 degrees F.

53. A method for collapsing steam from a steam sterilizer comprising:
providing a steam sterilizer configured to discharge steam;
providing a container comprising a chamber for holding fluid, a receiving port, an outlet port, and a tube extending from said receiving port into said chamber;
providing said fluid to said chamber;
receiving at least steam from the steam sterilizer through said tube for collapsing said at least steam with said fluid;
sensing a temperature of said fluid;
providing additional fluid to said chamber in response to the sensed temperature of said chamber to cool the chamber, after the chamber having at least reached a predetermined temperature; and
allowing at least some fluid to move out of said chamber through said outlet port.

54. The method of claim 53, wherein providing additional fluid to said chamber comprises:
causing a valve to control the flow of said additional fluid into said chamber based on said sensed temperature.

55. The method of claim 54, wherein causing said valve to control the flow of additional fluid into said chamber includes opening said valve when said sensed temperature has reached at least a predetermined temperature.

56. The method of claim 55, wherein causing said valve to control the flow of additional fluid into said chamber includes closing said valve when said sensed temperature is below said predetermined temperature.

57. The method of claim 56, wherein said additional fluid includes water.

58. The method of claim 55, wherein said predetermined temperature is approximately 140 degrees F.

59. The method of claim 53, wherein sensing the temperature of the chamber includes continuously sensing the temperature of the fluid in said chamber.

60. The method of claim 53 additionally comprising:
providing said fluid to said chamber prior to receiving said at least steam in said chamber through said receiving port.

61. The method of claim 60, wherein said fluid includes water.

62. A system for collapsing steam comprising:
a steam sterilizer configured to discharge steam;
a container configured to hold fluid, the container including an uppermost point and a lowermost point;
at least one receiving port in the container to receive the steam from the steam sterilizer;
a conduit extending from the receiving port into the container configured to convey the steam to the fluid to collapse the steam;
a temperature probe extending into the container configured to sense a temperature of the fluid;
at least one inlet port in the container;
a valve in communication with the at least one inlet port, the valve configured to control the flow of additional fluid through the at least one inlet port into the container in response to the temperature, wherein said temperature probe is in communication with said valve; and
at least one drain port configured to drain at least some fluid from the container, said at least one drain port is intermediate said uppermost point and said lowermost point to determine a fluid level in the container.

63. A system for collapsing steam comprising:
a steam sterilizer configured to discharge steam;
a container configured to hold fluid;
at least one receiving port in the container;
a conduit extending from the receiving port into the container configured to convey at least some of the steam to the fluid to collapse the at least some steam;
a temperature probe extending into the container configured to sense a temperature of the fluid;
at least one inlet port in the container;
a valve configured to control the flow of additional fluid through the at least one inlet port into the container in response to the temperature; and
at least one drain port configured to drain at least some fluid from the container.

* * * * *